(12) United States Patent
Kurfurst et al.

(10) Patent No.: US 7,087,743 B2
(45) Date of Patent: Aug. 8, 2006

(54) OLIGONUCLEOTIDES AND USE OF OLIGONUCLEOTIDES MODULATING THE EXPRESSION OF ENZYMES INVOLVED IN THE SYNTHESIS OF MELANIC PIGMENTS, AS DEPIGMENTATION AGENTS

(75) Inventors: Robin Kurfurst, Olivet (FR); Régine Joly, Autheux (FR)

(73) Assignee: LVMH Recherche, Paris (FR)

( * ) Notice: Subject to any disclaimer, the term of this patent is extended or adjusted under 35 U.S.C. 154(b) by 229 days.

(21) Appl. No.: 10/203,398

(22) PCT Filed: Feb. 9, 2001

(86) PCT No.: PCT/FR01/00398

§ 371 (c)(1),
(2), (4) Date: Jan. 6, 2003

(87) PCT Pub. No.: WO01/58918

PCT Pub. Date: Aug. 16, 2001

(65) Prior Publication Data

US 2004/0014700 A1    Jan. 22, 2004

(30) Foreign Application Priority Data

Feb. 11, 2000   (FR) .................................. 00 01730

(51) Int. Cl.
*C07H 21/04*   (2006.01)
*A61K 48/00*   (2006.01)
*C12Q 1/68*    (2006.01)

(52) U.S. Cl. ...................... 536/24.5; 536/23.1; 514/44; 435/6; 435/325; 435/375

(58) Field of Classification Search ............... 536/23.1, 536/24.6; 514/44
See application file for complete search history.

(56) References Cited

U.S. PATENT DOCUMENTS 5,679,511 A * 10/1997 Kwon ........................... 435/6
5,948,680 A *  9/1999 Baker et al. ................. 435/375

FOREIGN PATENT DOCUMENTS

EP         0714907 A1  *  6/1996
WO         WO 9714709  *  4/1997

OTHER PUBLICATIONS

O'Connell et al. Clinical Chemistry 1998, vol. 44, pp. 1161-1169.*
Giebel et al. Genbank Accession No. M63235, Jan. 1995.*

* cited by examiner

*Primary Examiner*—J. D. Schultz
*Assistant Examiner*—Tracy Vivlemore
(74) *Attorney, Agent, or Firm*—Blakely Sokoloff Taylor & Zafman

(57) ABSTRACT

The present invention relates to novel oligonucleotide sequences and also to derivatives thereof.

These novel oligonucleotide sequences are capable of hybridizing specifically with the gene or with a product of the gene encoding tyrosinase, or with the gene or a product of the gene encoding tyrosinase-related-protein 1 (TRP-1).

The present invention also relates to the use of these novel oligonucleotide sequences as a depigmenting or bleaching agent in a cosmetic composition or in a dermatological composition.

24 Claims, No Drawings

OLIGONUCLEOTIDES AND USE OF OLIGONUCLEOTIDES MODULATING THE EXPRESSION OF ENZYMES INVOLVED IN THE SYNTHESIS OF MELANIC PIGMENTS, AS DEPIGMENTATION AGENTS

This is a non-provisional application claiming the benefit of International application number PCT/FR01/00398 filed Feb. 9, 2001.

The present invention relates to novel oligonucleotide sequences and also to derivatives thereof.

These novel oligonucleotide sequences are capable of hybridizing with the gene or with a product of the gene encoding one of the essential enzymes involved in the synthetic pathway for melanin pigments.

The present invention also relates to the use of these novel oligonucleotide sequences as depigmenting or bleaching agents for the skin in a cosmetic composition or in a dermatological composition.

In humans, pigmentation results from the synthesis and distribution of melanin pigments in the skin, the hair follicles or the eyes. The pigmentation is genetically predefined but it is regulated by many internal or external factors. The melanins produced by melanocytes and also the number of melanocytes, their tyrosinase activity and their capacity to export melanins to keratinocytes, and the size of the melanosomes which contain melanin grains will condition the colour of human skin. For each individual, the colour of the skin varies mainly as a function of the more or less significant amount of radiation from ultraviolet (UV) rays. In other words, for each individual, there exists a basic skin pigmentation when he is subjected to the weakest amount of UV radiation, which corresponds to his palest skin colour, and a more intense skin pigmentation if he receives a stronger amount of UV radiation, ranging up to a maximum pigmentation which corresponds to his darkest skin colour when he is exposed for a sustained period to intense UV radiation such as that which may be encountered at altitude in the mountains.

In addition, as is well known, there exists in the world population a very great genetic diversity regarding skin pigmentation. Thus, depending on the population, the skin colour corresponding to the basic pigmentation defined above shows a paler or darker complexion which lies between the two extremes: very pale and very dark. Also depending on the population, the difference in skin complexion between the basic pigmentation and the maximum pigmentation is more or less significant. Thus, it is well known that individuals belonging to certain populations with pale skin (basic pigmentation) react rapidly and/or significantly to the action of UV radiation and can therefore easily have a dark skin complexion, even when these individuals have not deliberately exposed themselves to the sun for a sustained period of time. In the remainder of the text, these individuals will be denoted by the expression "individuals who are very reactive to UV radiation". This is especially the case for populations of Asian origin or for certain populations termed mixed-race populations.

Furthermore, individuals witness the appearance of darker or more coloured areas or blemishes on their skin, in particular on the face and hands, which gives the skin a certain heterogeneity. These blemishes are due to a considerable concentration of melanin in the keratinocytes of the epidermis.

The mechanism of formation of skin pigmentation involves the synthesis of melanins. This mechanism is particularly complex and schematically involves the following main steps:

Tyrosine➙Dopa➙Dopaquinone➙Dopachrome➙Melanins

The enzymes known to be involved in this series of reactions are essentially tyrosinase and tyrosinase-related-protein 1 (TRP-1). These enzymes in particular catalyse the reaction of transformation of tyrosine to dopa (dihydroxyphenylalanine) and the reaction of transformation of dopa to dopaquinone, leading to the formation of melanin pigments. These enzymes do not become involved individually during the reaction mechanism of melanogenesis. In fact, tyrosinase and TRP-1 form an enzymatic complex (Winder et al. (1994) Cell. Mol. Biol. Res. 40: 7–8; Orlow et al. (1994) J. of Investigative Dermatology 103: 196–211). These two enzymes therefore act in concert and it appears that they never function without one another. It is known that, when a cell is TRP-1-depleted, a loss of tyrosinase activity is observed (Orlow et al. (1994)); this means that, in order to be active, tyrosinase requires the presence of TRP-1 (Zhao et al. (1996) J. of Investigative Dermatology 106: 744–752).

In the remainder of the present text, these essential enzymes involved in the synthetic pathway for melanins will be denoted by the expression "enzymes essential for pigmentation".

A molecule is acknowledged to be a depigmenting molecule if it acts directly on the epidermal melanocytes by inhibiting the activity of these cells and/or if it blocks one of the steps of melanin biosynthesis. This is in particular the case when the molecule inhibits one of the enzymes involved in melanogenesis or when it reacts with the chemical compounds of the melanin synthesis chain.

Known depigmenting substances are in particular hydroquinone and derivatives thereof, ascorbic acid and derivatives thereof, placental extracts, kojic acid, ferulic acid, arbutin, dihydroxybenzene derivatives (WO 00/47045), guaiacol derivatives (WO 00/47179), 4-(2,3-dihydroxyphenyl)cyclohexanol (WO 00/56279), resorcinol derivatives (WO 00/56702) and phenol amides (WO 99/32077). These substances can have certain drawbacks. They may be unstable, require use at high concentrations, lack specificity regarding their mode of action or have a cytotoxic or irritant power.

The topical use of effective and harmless depigmenting substances is particularly desired in cosmetics and in dermatology. The substances are in particular used for treating regional hyper-pigmentations due to melanocytic hyperactivity, such as idiopathic melasmas, localized hyperpigmentations due to benign melanocytic hyperactivity and proliferation, such as pigmentary blemishes known as senescent pigmentary blemishes (senile lentigo), accidental hyperpigmentations, such as photosensitization or cicatricial hyperpigmentation, and certain leukodermias, such as vitiligo. In the latter cases, since it is not possible to repigment the skin, the pigmentation around the edges of the depigmented areas is attenuated so as to give the skin a more homogeneous colour.

Depigmenting substances are also used as bleaching agents for the skin by certain individuals, in particular those denoted above, who are very reactive to UV radiation, in order to lighten their complexion, in particular that of their face and of their hands, so as to conserve as pale or as homogeneous a skin colour as possible, or at the very least to reduce the pigmenting effects of UV rays.

The problem which confronts the professionals is therefore the design, manufacture or isolation of novel depigmenting substances or of novel bleaching agents for human skin, for body hair or for head hair which do not have the drawbacks of known substances, i.e. which are non-irritant, non-toxic and/or non-allergenic for the skin, and which are stable in a composition.

The use of an antisense oligonucleotide for treating diseases due to melanocyte dysfunction, in particular vitiligo and other depigmenting diseases, has been described in WO 99/25819. In these pathological skin conditions, the hypopigmentation results from an abnormally high tenascin content. The oligonucleotides described in that document act against hypopigmentation by regulating tenascin expression.

On the other hand, the object of the present invention consists in providing a depigmenting agent which acts on the process of melanogenesis, and which is intended firstly, in the case of substantially homogeneous pigmentation, to bleach the skin, body hair or head hair, i.e. to decrease their pigmentation, and secondly, to combat hyperpigmentation of the skin, i.e. when the skin shows heterogeneous pigmentation.

The inventors of the present invention have found that oligonucleotides can hybridize with the genes or the products of the gene (such as RNAs) encoding the enzymes essential for pigmentation.

Thus, the oligonucleotides according to the invention, in modulating the expression of the enzymes essential for pigmentation in melanocytes, are involved upstream of the melanogenesis reaction given above. This activity exists even at very low concentration, which increases the advantage of these oligo-nucleotides. In addition, the oligonucleotides according to the invention show no cytotoxicity.

The oligonucleotides according to the invention offer an ideal solution to the problems posed by the substances conventionally used. The known substances which inhibit the activity of tyrosinase or of TRP-1 (in particular hydroquinone and derivatives thereof, ascorbic acid and derivatives thereof, placental extracts, kojic acid and arbutin), have many unacceptable side effects due to their poor specificity. The present invention therefore resolves the problems encountered by previous researchers by modulating the production of the enzymes essential for pigmentation, instead of directly inhibiting the enzymes, in order to obtain the depigmenting effect.

Since the essential enzymes function in concert in the form of a complex, the inventors have described novel oligonucleotides which inhibit the expression of one or other of the enzymes of the complex in order to resolve the problem posed.

The oligonucleotides according to the invention are novel per se and novel as medicinal products.

The present invention relates to an oligonucleotide comprising a number of nucleotides of between 7 and 25, preferably between 9 and 25, between 12 and 25, between 15 and 25 or between 18 and 25, and more preferably comprising a number equal to 20, capable of hybridizing with the gene or a product of the gene encoding one of the enzymes essential for pigmentation. In particular, said oligonucleotide is capable of hybridizing with the gene or a product of the gene encoding tyrosinase, or with the gene or a product of the gene encoding tyrosinase-related-protein 1 (TRP-1).

The present invention more particularly relates to an oligonucleotide which is defined above and which is capable of hybridizing specifically with the gene or a product of the gene encoding tyrosinase, or with the gene or a product of the gene encoding TRP-1.

In particular, it is an oligonucleotide, the sequence of which is chosen from the sequences SEQ ID NO. 1 TO SEQ ID NO. 11 which signify the following:

```
5'-GCAAAACAAAGACCTGGTTT-3'      SEQ ID NO.1

5'-AGACCTGGTTTGCAGCTCTT-3'      SEQ ID NO.2

5'-TGCTTGAAATAAGAGTGCAA-3'      SEQ ID NO.3

5'-AAAATCCAGCTCACAATCCT-3'      SEQ ID NO.4

5'-AGGAGCACTCATTCTGCTTG-3'      SEQ ID NO.5

5'-AGGAACTGGCTAATTGGAGT-3'      SEQ ID NO.6

5'-CAAGGTCTGCAGGAACTGGC-3'      SEQ ID NO.7

5'-CCTCACAAGGTCTGCAGGAA-3'      SEQ ID NO.8

5'-CTACAGACAATCTGCCAAGA-3'      SEQ ID NO.9

5'-GCATTCTTCCTCTAGTCCTC-3'      SEQ ID NO.10

5'-TTCCAGTACCTCACAATCCT-3'      SEQ ID NO.11
```

A subject of the present invention is also an oligonucleotide as a novel product, the sequence of which is one of the sequences SEQ ID NO. 1 to SEQ ID NO. 11 described above.

In the context of the present invention, the expression "gene encoding tyrosinase" is intended to mean the genomic sequence of the tyrosinase gene. Similarly, the expression "gene encoding TRP-1" is intended to mean the genomic sequence encoding the TRP-1 gene.

The key roles of tyrosinase and of TRP-1 in melanogenesis are known. The use of oligonucleotides directed against a messenger RNA encoding an enzyme or a protein in order to modulate the expression thereof is also known. However, the technique developed by the inventors of the present invention has never been used as a means of depigmentation.

The oligonucleotides according to the invention are determined so as to hybridize directly with the messenger RNA or with the gene. They thus make it possible to carry out an ultimate modulation of the amount of tyrosinase or of TRP-1 produced by the genes.

In the present document, the term "hybridization" is used to denote the formation of hydrogen bonds, also known as Watson-Crick pairing, between the complementary bases, conventionally on two strands of nucleic acid so as to form a duplex in the form of a double helix.

The degree of complementarity between two nucleic acid sequences of identical length is determined by comparing, after alignment, the first sequence with the sequence complementary to the second sequence. The degree of complementarity is calculated by determining the number of identical positions for which the nucleotide is identical between the two sequences thus compared, dividing this number of identical positions by the total number of positions and multiplying the result obtained by 100 so as to obtain the degree of complementarity between these two sequences.

The term "specific hybridization" means in particular that a degree of complementarity exists which is sufficient to avoid the nonspecific attachment of the oligonucleotide to a non-targeted sequence under the conditions in which the specific attachment is desired. It is understood that the oligonucleotide does not need to have 100% complementarity with the sequence of the target nucleic acid in order to hybridize specifically. In particular, an oligonucleotide having a degree of complementarity at least equal to approximately 80% is capable of hybridizing specifically with the nucleic acid chosen as the target.

The oligonucleotides according to the invention preferably hybridize specifically with the genes or the products of the genes encoding the enzymes essential for pigmentation. In particular, the oligonucleotides of the invention are capable of hybridizing either with the DNA of the gene which encodes tyrosinase or with the DNA of the gene which encodes TRP-1, or alternatively with the mRNA derived from one or other of these genes. The oligonucleotides according to the invention comprise a number of nucleotides sufficient in identity and in number to hybridize specifically. This property is commonly termed "antisense".

A subject of the present invention is therefore oligonucleotides which hybridize specifically upstream of, or to, the coding region of the gene concerned, or alternatively to the region exhibiting the initiation codon for translation of this gene.

The subject of the present invention is also oligonucleotides which hybridize specifically with either the DNA or the messenger RNA which encodes one of the enzymes essential for pigmentation, in particular tyrosinase or TRP-1.

The subject of the present invention is also oligonucleotides which hybridize specifically either with the 5' noncoding region, with the region exhibiting the initiation codon, with the coding region or with the 3' noncoding region of the gene or of the mRNA encoding one of the enzymes essential for pigmentation, in particular tyrosinase or TRP-1.

In the context of the present invention, the expression "DNA which encodes tyrosinase" or "DNA which encodes TRP-1" is intended to mean both the exons and the introns, in particular the exons.

It is specified that:
  the oligonucleotides of the invention of sequences SEQ ID NO. 1, SEQ ID NO. 2, SEQ ID NO. 3 and SEQ ID NO. 4 hybridize specifically with the 5' noncoding region of the gene or of the mRNA encoding TRP-1,
  the oligonucleotide of the invention of sequence SEQ ID NO. 5 hybridizes specifically with the region exhibiting the initiation codon of the gene or of the mRNA encoding TRP-1,
  the oligonucleotides of the invention of sequences SEQ ID NO. 6, SEQ ID NO. 7 and SEQ ID NO. 8 hybridize specifically with the 5' noncoding region of the gene or of the mRNA encoding tyrosinase,
  the oligonucleotide of the invention of sequence SEQ ID NO. 9 hybridizes specifically with the coding region of the gene or of the mRNA encoding tyrosinase,
  the oligonucleotide of the invention of sequence SEQ ID NO. 10 hybridizes specifically with the region exhibiting the initiation codon of the gene or of the mRNA encoding tyrosinase,
  the oligonucleotide of the invention of sequence SEQ ID NO. 11 hybridizes specifically with the 5' noncoding region of the gene or of the mRNA encoding TRP-1.

A subject of the present invention is also oligonucleotides comprising one or more chemical modifications to their sugar components, their nucleobase components or their internucleotide backbone, which confer desirable physicochemical characteristics on the oligonucleotides according to the invention, such as increased bioavailability, an increase in the affinity for the target sequences, an increase in cellular internalization, or better biological stability or an increase in stability in the presence of cellular nucleases.

By way of example, the modifications which can confer these characteristics are 2'—O-alkyl and 2'—O-fluoro derivatives on the sugar component of the nucleoside, and phosphorothioate derivatives or methyl phosphonate derivatives within the internucleotide backbone.

In the present document, the term "oligonucleotide" refers to polynucleotides made from natural nucleobases and from pentafuranosyl (sugar) groups which form nucleosides which are connected to one another via native phosphodiester linkages. The term "oligonucleotides" therefore refers to the natural species or to the synthetic species made from natural subunits or from close homologues thereof.

The term "oligonucleotides" may also refer to the components which have functions similar to the natural oligonucleotides but which may have unnatural portions. The oligonucleotides may have modified sugar components, modified nucleobase components or modified internucleotide linkages. Among possible modifications, the preferred modifications are 2'—O-alkyl derivatives on the sugar component, in particular 2'—O-ethyloxy-methyl or 2'—O-methyl derivatives, or phosphorothioates or methyl phosphonates for the internucleotide backbone.

Chimeric oligonucleotides are included in the preferential modifications of the invention. The oligonucleotides contain at least two chemically different regions, each comprising at least one nucleotide. It involves in particular one or more regions comprising a modified nucleotide which confers one or more beneficial properties such as, for example, better biological stability, increased bioavailability, an increase in cellular internalization or an increase in the affinity for the target RNA.

Preferably, the internucleotide backbone can consist entirely or partly of phosphodiesters, phosphorothioates or methyl phosphonates, or combinations of phosphodiester and/or phosphorothioate and/or methyl phosphonate linkages.

Thus, the oligonucleotide according to the invention is characterized in that some of the phosphodiester groups of its internucleotide backbone are replaced with phosphorothioate groups and/or methyl phosphonate groups.

Alternatively, the oligonucleotide according to the invention is characterized in that all the phosphodiester groups are replaced with phosphorothioate groups or with methyl phosphonate groups.

Alternatively, the phosphodiester groups are entirely or partly replaced with phosphorothioate groups and/or methyl phosphonate groups.

The term "oligonucleotides" may also refer to oligonucleotides onto which a circular administration vector of the plasmid type or a linear administration vector of the nucleic acid or peptide type has been grafted.

The oligonucleotides of the invention are novel as medicinal products.

A subject of the present invention is also a cosmetic or dermatological composition containing at least one oligonucleotide described above and a cosmetically or dermatologically acceptable medium. Such a composition may also contain one or more active agents intended to reinforce the desired effects.

A subject of the present invention is also the use of at least one oligonucleotide sequence directed against a product of transcription of the gene encoding one of the enzymes essential for pigmentation, in particular tyrosinase or TRP-1, in or for the manufacture of a cosmetic or dermatological composition for depigmenting or bleaching human skin, body hair or head hair, or removing or attenuating pigmentary blemishes on human skin.

The present invention also relates to the use of an oligonucleotide capable of hybridizing specifically with the gene or a product of the gene encoding one of the enzymes essential for pigmentation, in particular tyrosinase or TRP-1, as a cosmetic agent, in particular for depigmenting or bleaching human skin, body hair or head hair, and for attenuating pigmentary blemishes on human skin.

A subject of the present invention is also the use of at least one oligonucleotide sequence directed against a product of transcription of the gene encoding one of the enzymes essential for pigmentation, in particular tyrosinase or TRP-1, in or for the manufacture of a cosmetic or dermatological composition as an inhibitor of melanin synthesis.

The present invention also relates to the use of at least one oligonucleotide described above for the manufacture of a medicinal product intended for the treatment or for the prevention of diseases resulting in the overexpression of tyrosinase and/or TRP-1, via the topical route. This medicinal product may be intended for inhibiting melanin synthesis, in particular for depigmenting or for bleaching the skin, but also for the treatment or the prevention of regional hyperpigmentations due to melanocytic hyperactivity, such as idiopathic melasmas, of localized hyperpigmentations due to benign melanocytic hyperactivity and proliferation, such as senescent pigmentary blemishes (senile lentigo), and of accidental hyperpigmentations, such as photo-sensitization or post-lesional scarring, and for the treatment of certain leukodermias, such as vitiligo.

A subject of the present invention is also the use of at least one oligonucleotide sequence directed against a product of transcription of the gene encoding one of the enzymes essential for pigmentation, in particular tyrosinase or TRP-1, in a depigmenting or bleaching cosmetic composition for human skin.

The present invention also relates to the use of the oligonucleotides described above for modulating the expression of one of the enzymes essential for pigmentation, in particular tyrosinase or TRP-1.

A subject of the present invention is also the use of at least one oligonucleotide sequence directed against a product of transcription of the gene encoding one of the enzymes essential for pigmentation, in particular tyrosinase or TRP-1, for the manufacture of a depigmenting or bleaching dermatological composition for human skin.

The present invention also relates to a cosmetic or dermatological treatment process for depigmenting or bleaching human skin, consisting in applying, to the pigmented skin, a cosmetic composition comprising at least one oligonucleotide sequence directed against a product of transcription of the gene encoding one of the enzymes essential for pigmentation, in particular tyrosinase or TRP-1.

A subject of the present invention is also a depigmenting composition, characterized in that it contains, in a cosmetically or dermatologically acceptable medium, at least one oligonucleotide sequence directed against a product of transcription of the gene encoding one of these enzymes essential for pigmentation, in particular tyrosinase or TRP-1.

According to a preferred embodiment of the present invention for the abovementioned compositions, uses and treatment process, the oligonucleotides are those the sequence of which is one of those defined below:

| | |
|---|---|
| 5'-GCAAAACAAAGACCTGGTTT-3' | SEQ ID NO.1 |
| 5'-AGACCTGGTTTGCAGCTCTT-3' | SEQ ID NO.2 |

-continued

| | |
|---|---|
| 5'-TGCTTGAAATAAGAGTGCAA-3' | SEQ ID NO.3 |
| 5'-AAAATCCAGCTCACAATCCT-3' | SEQ ID NO.4 |
| 5'-AGGAGCACTCATTCTGCTTG-3' | SEQ ID NO.5 |
| 5'-AGGAACTGGCTAATTGGAGT-3' | SEQ ID NO.6 |

The cosmetic or dermatological composition according to the invention is suitable for topical use and therefore contains a cosmetically or dermatologically acceptable medium, i.e. a medium compatible with the skin. The oligonucleotide sequence according to the invention may be present in an amount ranging from 0.00001% to 10% and preferably from 0.0003% to 3% of the total weight of the composition.

The composition of the invention may be provided in all the pharmaceutical forms conventionally used for topical application, in particular in the form of an aqueous, aqueous-alcoholic or oily solution, of an oil-in-water, water-in-oil or multiple emulsion, of an aqueous or oily gel, of a liquid, pasty or solid anhydrous product, of a dispersion of polymeric particles, such as nanospheres and nanocapsules, in an aqueous or oily phase, or of a dispersion of lipid vesicles of the ionic or nonionic type as described in U.S. Pat. No. 4,508,703.

This composition may be more or less fluid and may have the appearance of a white or coloured cream, an ointment, a milk, a gel, a lotion, a serum, a paste or a mousse. It may optionally be applied to the skin in the form of an aerosol. It may also be provided in solid form, which may or may not be pulverulent, for example in the form of a stick or a compacted powder. It may also be provided in the form of patches, of pencils, of brushes and of applicators which allow localized application on the blemishes of the face or of the hands. It may be used as a care product or as a make-up product.

In a known manner, the composition of the invention may also contain the adjuvants which are common in cosmetics and dermatology, such as hydrophilic or lipophilic gelling agents, hydrophilic or lipophilic active agents, preserving agents, antioxidants, solvents, fragrances, fillers, screening agents, pigments, odour absorbers and dyestuffs. The amounts of these various adjuvants are those conventionally used in the fields under consideration. Depending on their nature, these adjuvants may be introduced into the fatty phase, into the aqueous phase, into the lipid vesicles or into the nanoparticles.

When the cosmetic or dermatological composition of the invention is an emulsion, the proportion of the fatty phase may range, in general, from 5 to 80% by weight, and preferably from 5 to 50% by weight relative to the total weight of the composition. The oils, the emulsifiers and the co-emulsifiers used in the composition in emulsion form are chosen from those conventionally used in the field under consideration. The emulsifier and the co-emulsifier are present in the composition in a proportion generally ranging from 0.3% to 30% by weight, and preferably from 0.5% to 20% by weight relative to the total weight of the composition.

As oils which may be used in combination with the oligonucleotides according to the invention, mention may be made of mineral oils (liquid petroleum jelly), oils of plant origin (avocado oil, soyabean oil), oils of animal origin (lanolin), synthetic oils (perhydrosqualene), silicone oils (cyclomethicone) and fluoro oils (perfluoropolyethers).

Fatty alcohols (cetyl alcohol), fatty acids and waxes (carnauba wax, ozokerite) may also be used as fatty substances.

As emulsifiers and co-emulsifiers which may be used in combination with the oligonucleotides according to the invention, mention may be made, for example, of fatty acid esters of polyethylene glycol, such as PEG-20 stearate, and fatty acid esters of glycerol, such as glyceryl stearate.

As hydrophilic gelling agents which may be used in combination with the oligonucleotides according to the invention, mention may be made in particular of carboxyvinyl polymers (carbomer), acrylic copolymers, such as acrylate/alkylacrylate copolymers, poly-acrylamides, polysaccharides, natural gums and clays. As lipophilic gelling agents, mention may be made of modified clays such as bentones, metal salts of fatty acids, hydrophobic silica and polyethylenes.

A subject of the present invention is a cosmetic or dermatological composition containing at least one oligonucleotide described above and one or more other active agents.

The present invention also relates to the use of at least one oligonucleotide as described above for the manufacture of a medicinal product intended to be administered simultaneously or separately or in a way which is spread out over time, in combination with one or more active agents.

Said active agents which may be used in combination with the oligonucleotides according to the invention, and which are used pure or originate from extracts containing these molecules, are in particular the following compounds: ellagic acid and derivatives thereof; hydroquinone; arbutin; resorcinol and derivatives thereof; vitamin C and derivatives thereof; pantothenate sulphonate and derivatives thereof; kojic acid; placental extracts; molecules which interfere directly or indirectly with alpha-melanocyte-stimulating hormone (α-MSH) or its receptor or adreno-corticotropic hormone (ACTH); polyols, such as glycerol, glycol or propylene glycol; vitamins; keratolytic or desquamating agents, such as salicylic acid and derivatives thereof; α-hydroxy acids, such as lactic acid or malic acid, alone or grafted; ascorbic acid and derivatives thereof; retinoic acid; retin-aldehyde; retinol and derivatives thereof, such as palmitate, propionate or acetate, which may or may not be in a liposomal preparation; antiglycation agents or antioxidants, taken alone or in combination, such as tocopherol and derivatives thereof, thiotaurine, hypotaurine, aminoguanidine, thiamine pyrophosphate, pyridoxamine, lysine, histidine, arginine, phenyl-alanine, pyridoxine, adenosine triphosphate; anti-inflammatory agents, such as stearyl glycyrrhetinate; soothing agents and mixtures thereof, chemical or physical sunscreens, such as micronized zinc oxide, titanium oxide, butylmethoxydibenzoylmethane and octyl methoxycinnamate; and deoxyribonucleic or nucleic acids. In the event of incompatibility, these other active agents and/or the oligonucleotides of the invention may be incorporated into spherules, in particular vesicles made of ionic or nonionic amphiphilic lipids as described in U.S. Pat. No. 4,508,703, or nanoparticles.

The following examples illustrate the present invention without, however, limiting it.

For reasons of stability in the in-vitro culture media and in accordance with common practice, Examples 2 to 4 were carried out with phosphorothioate derivatives and Examples 5 to 12 were prepared equally with phosphorothioate or phosphodiester derivatives.

In the following examples, all the percentages are given by weight, unless otherwise stated.

EXAMPLE 1

Oligonucleotide Synthesis

By way of examples, oligonucleotides were synthesized with an automatic synthesizer (Perseptive Biosystems Expedite model 8909) by standard phosphoramidite derivative chemistry, using the manufacturer's protocols. The β-cyanoethyldiisopropyl-phosphoramidites were supplied by the company Perseptive Biosystems. For the phosphodiester oligonucleotides, the phosphite oxidation step was performed with an iodine solution. With regard to the phosphorothioate oligonucleotides, the phosphite oxidation step was performed using a 0.05 M solution of 3H-1,2-benzodithiol-3-one 1,1-dioxide in anhydrous acetonitrile. After cleavage from the column (Controlled Pore Glass, Perseptive Biosystems) and total deprotection of the sequence by treatment for 18 h at 55° C. with a 33% aqueous ammonia solution, the oligonucleotides were purified by precipitation in ethanol in the presence of sodium acetate. High pressure liquid chromatography controls have been carried out by ion exchange chromatography with elution using a sodium chloride gradient and by C18 reverse phase chromatography with elution using a gradient of acetonitrile in the presence of triethylammonium acetate.

The oligonucleotides synthesized are described in Table 1. They are the first 11 sequences of this table, numbered from SEQ ID NO. 1 to SEQ ID NO. 11. Their depigmenting activity was the subject of studies reported in the following examples.

In Table 1, the numbers given under each end of the sequences indicate the position of the oligonucleotide in the sequences of origin.

The sequences originate, respectively, from the sequence termed "HUMTYRA" of the human tyrosinase cDNA, published by Shibahara et al., Tohoku J. Exp. Med. 156: 403 (1988) (Genbank accession number M 27160) from the sequence termed "HSTYRRP" of the human TRP-1 cDNA, published by Cohen et al., Nucl. Acides Res. 18: 2807 (1990) (Genbank accession number X 51420) and from another sequence of TRP-1, termed "AF001295", published by Box et al., Mamm. Genome 9: 50 (1998) (Genbank accession number AF 001295).

Moreover, by way of comparison in order to confirm the specificity of the oligonucleotides according to the invention with respect to the genes or to the products of genes encoding tyrosinase or TRP-1, two oligonucleotides based on the sequence SEQ ID NO. 2 of the invention were synthesized, namely:

❖ A sequence termed "sense control", denoted SEQ ID NO. 12 in Table 1, consisting in reversing the order of the bases of the sequence SEQ ID NO. 2.

❖ A sequence termed "scrambled control", denoted SEQ ID NO. 13, also in Table 1, comprising the same bases, in nature and in number, as those of the sequence SEQ ID NO. 2, but placed in any order.

TABLE 1

| SEQ ID NO. | | OLIGONUCLEOTIDE SEQUENCE | | LOCUS |
|---|---|---|---|---|
| 1. | 111 | 5'-GCAAAACAAAGACCTGGTTT-3' | 92 | HSTYRRP |
| 2. | 102 | 5'-AGACCTGGTTTGCAGCTCTT-3' | 83 | HSTYRRP |
| 3. | 127 | 5'-TGCTTGAAATAAGAGTGCAA-3' | 108 | HSTYRRP |
| 4. | 53 | 5'-AAAATCCAGCTCACAATCCT-3' | 34 | HSTYRRP |

TABLE 1-continued

| SEQ ID NO. | | OLIGONUCLEOTIDE SEQUENCE | | LOCUS |
|---|---|---|---|---|
| 5. | 141 | 5'-AGGAGCACTCATTCTGCTTG-3' | 122 | HSTYRRP |
| 6. | 475 | 5'-AGGAACTGGCTAATTGGAGT-3' | 457 | HUMTYRA |
| 7. | 485 | 5'-CAAGGTCTGCAGGAACTGGC-3' | 466 | HUMTYRA |
| 8. | 490 | 5'-CCTCACAAGGTCTGCAGGAA-3' | 471 | HUMTYRA |
| 9. | 1332 | 5'-CTACAGACAATCTGCCAAGA-3' | 1313 | HUMTYRA |
| 10 | 506 | 5'-GCATTCTTCCTCTAGTCCTC-3' | 487 | HUMTYRA |
| 11. | 5875 | 5'-TTCCAGTACCTCACAATCCT-3' | 5856 | AF001295 |
| 12. | | 5'-TTCTCGACGTTTGGTCCAGA-3' | | SENSE CONTROL SEQ ID NO.2 |
| 13. | | 5'-ACGTTTCTCGCCTAGTGATG-3' | | SCRAMBLED CONTROL SEQ ID NO.2 |
| 1. | 111 | 5'-GCAAAACAAAGACCTGGTTT-3' | 92 | HSTYRRP |
| 2. | 102 | 5'-AGACCTGGTTTGCAGCTCTT-3' | 83 | HSTYRRP |
| 3. | 127 | 5'-TGCTTGAAATAAGAGTGCAA-3' | 108 | HSTYRRP |
| 4. | 53 | 5'-AAAATCCAGCTCACAATCCT-3' | 34 | HSTYRRP |
| 5. | 141 | 5'-AGGAGCACTCATTCTGCTTG-3' | 122 | HSTYRRP |
| 6. | 475 | 5'-AGGAACTGGCTAATTGGAGT-3' | 457 | HUMTYRA |
| 7. | 485 | 5'-CAAGGTCTGCAGGAACTGGC-3' | 466 | HUMTYRA |
| 8. | 490 | 5'-CCTCACAAGGTCTGCAGGAA-3' | 471 | HUMTYRA |
| 9. | 1332 | 5'-CTACAGACAATCTGCCAAGA-3' | 1313 | HUMTYRA |
| 10 | 506 | 5'-GCATTCTTCCTCTAGTCCTC-3' | 487 | HUMTYRA |
| 11. | 5875 | 5'-TTCCAGTACCTCACAATCCT-3' | 5856 | AF001295 |
| 12. | | 5'-TTCTCGACGTTTGGTCCAGA-3' | | CONTROLE SENS SEQ ID NO.2 |
| 13. | | 5'-ACGTTTCTCGCCTAGTGATG-3' | | CONTROLE BROUILLE SEQ ID NO.2 | reduction of the formation of melanin pigments and therefore to a depigmenting effect.

Preparation of Melanocyte Cultures and Treatments with the Oligonucleotides:

The melanocytes are obtained from the foreskin of a child of Caucasian type. The skin fragments are rinsed with PBS (Gibco, Paisley, GB), and then with 70% ethanol. After a final wash with PBS, the skin is cut up into fine 1 mm strips comprising a minimum of dermis. The dermis and the epidermis are dissociated by incubating the strips in a 0.25% trypsin solution (Gibco, Paisley, GB) overnight at 4° C. After incubation, the epidermal cells are recovered by scraping the cells with a scalpel. The action of the trypsin is stopped by placing the cells in E-199 medium (Gibco, Paisley, GB) containing 10% (V/V) of foetal calf serum (Gibco, Paisley, GB). After homogenization and elimination of the corneocytes floating at the surface, the cell suspension is filtered and centrifuged and the pellet is taken up in an adhesion medium (Medium 1), the composition of which is given in the following table, in which EGF denotes an epidermal growth factor.

COMPOSITION OF MEDIUM 1

| Compounds | Supplier, reference | Final concentration in the medium |
|---|---|---|
| E-199 medium | Gibco, 31150-022 | q.s. for 100% (v/v) |
| Foetal calf serum | Gibco, 10099-133 | 10% (v/v) |
| Hydrocortisone | Sigma, H-0135 | 0.4 µg/ml |
| L-glutamine | Gibco, 25030-024 | 2 mM |
| EGF | Sigma, E-4127 | 10 ng/ml |

After counting the cell population, the cells are seeded in flasks in a proportion of 200 000/cm². The cells are maintained at 37° C. in an atmosphere which is saturated with humidity, and with 5% $CO_2$. After the cells have adhered, the adhesion medium is replaced with KSFM medium (Gibco, Paisley, GB), which will be renewed every 48 h.

The epidermal cells thus placed in culture will make it possible to obtain a keratinocyte-melanocyte coculture. As soon as this coculture is at approximately 70% confluency, the KSFM medium is replaced with a selective medium (Medium 2) which promotes the growth of melanocytes and the composition of which appears in the table below, in which IBMX denotes 3-isobutyl-1-methylxanthine and PMA denotes phorbol 12-myristate 13-acetate.

COMPOSITION OF MEDIUM 2

| Compounds | Supplier, reference | Final concentration in the medium |
|---|---|---|
| E-199 medium | Gibco, 31150-022 | q.s. for 100% (v/v) |
| Foetal calf serum | Gibco, 10099-133 | 10% (v/v) |
| L-glutamine | Gibco, 25030-024 | 0.4 µg/ml |
| IBMX | Sigma, I-5879 | 2 mM |
| PMA | Sigma, P-8139 | 10 ng/ml |
| Geneticin | Gibco, 066-01811Y | 100 µg/ml |

48 to 72 h later, the cells are detached from the flask using a 0.1% trypsin-0.05% EDTA mixture (Gibco, Paisley, GB) for 1 to 2 minutes at room temperature. The cell suspension obtained is centrifuged and resuspended in selective medium. The cells are treated again 24 to 48 h later with the trypsin-EDTA (0.1%–0.05%) mixture, for 1 to 2 minutes at room temperature, and then re-seeded in a proliferation medium specific for melanocytes (Medium 3).

Medium 3 consists of 10% of Medium 2 and 90% of Medium A. Medium A is the keratinocyte medium SFM (Gibco, 17005-034).

At this stage, the cell population obtained is pure and consists exclusively of normal human melanocytes (NHMs).

Before the study, the NHMs are placed in a medium which contains no powerful metabolic activator, such as phorbol esters or IBMX (Medium 4), for a week.

Medium 4 consists of 10% of Medium B and 90% of Medium A described above. The composition of Medium B is described in the table below.

| COMPOSITION OF MEDIUM B | | |
|---|---|---|
| Compounds | Supplier, reference | Final concentration in the medium |
| E-199 medium | Gibco, 31150-022 | q.s. for 100% (v/v) |
| Foetal calf serum | Gibco, 10099-133 | 10% (v/v) |
| L-glutamine | Gibco, 25030-024 | 2 mM |

The NHMs are seeded in 96-well microplates (Falcon, Franklin Lakes, N.J., USA) in a proportion of 10 000 cells per well, in 200 µl of Medium 4.

The oligonucleotides to be tested are prepared extemporaneously in the study medium, at concentrations of 10 nM, 100 nM, 250 nM, 500 nM and 1 µM, respectively. The treatments with the various oligonucleotides are carried out every day for 7 days. For each concentration, 3 assays are performed.

Measurement of Reaction Rates for the Dopa Oxidase Activity:

At the end of these treatments divided up over 7 days, the tyrosinase or "dopa oxidase" activity is measured.

The cells are rinsed with PBS, then 50 l of lysis buffer (0.5% Triton X100 (Sigma, T-9284) in PBS (Gibco, 14190-094)) are added to the wells and the plate is shaken for one hour at 4° C. The reaction is initiated by adding 50 µl of substrate (10 mM L-DOPA, Sigma) to each well. The appearance of the dopachrome is measured at 450 nm every 2 minutes, for one hour and at 37° C., with regular shaking, using an optical density reader, the microplate reader 340 ATTC (SLT-Labinstrument, Grödig/Salzburg, Austria). The reaction rates are calculated and expressed as $10^{-4}$ OD units/min.

The results obtained for the cultures treated with the oligonucleotides and for the control (non-treated) cultures are given in Table 2 (σ: standard deviation).

TABLE 2

| Identification numbers and concentrations of the oligonucleotides tested | | Reaction rates $10^{-4}$ OD units/min | Reaction rates (control without oligonucleotide) | % variation compared to control |
|---|---|---|---|---|
| SEQ ID NO. 1 | 10 nM | 21.8 σ = 1.0 | 26.4 σ = 1.8 | −17.4 |
| | 100 nM | 23.3 σ = 0.4 | 26.4 σ = 1.8 | −11.7 |
| | 250 nM | 20.3 σ = 0.3 | 26.4 σ = 1.8 | −23.1 |
| | 500 nM | 19.5 σ = 2.9 | 26.4 σ = 1.8 | −26.1 |
| | 1 µM | 23.9 σ = 1.4 | 26.4 σ = 1.8 | −9.4 |
| SEQ ID NO. 2 | 10 nM | 20.5 σ = 1.7 | 26.4 σ = 1.8 | −22.3 |
| | 100 nM | 18.8 σ = 1.5 | 26.4 σ = 1.8 | −28.8 |
| | 250 nM | 19.2 σ = 0.7 | 26.4 σ = 1.8 | −27.3 |
| | 500 nM | 19.7 σ = 1.7 | 26.4 σ = 1.8 | −25.4 |
| | 1 µM | 22.9 σ = 1.1 | 26.4 σ = 1.8 | −13.3 |
| SEQ ID NO. 3 | 10 nM | 23.7 σ = 3.1 | 26.4 σ = 1.8 | −10.2 |
| | 100 nM | 20 σ = 0.7 | 26.4 σ = 1.8 | −24.2 |
| | 250 nM | 21.1 σ = 0.6 | 26.4 σ = 1.8 | −20.1 |
| | 500 nM | 19.9 σ = 1.7 | 26.4 σ = 1.8 | −24.6 |
| | 1 µM | 23.6 σ = 0.6 | 26.4 σ = 1.8 | −10.6 |
| SEQ ID NO. 4 | 10 nM | 22.9 σ = 1.2 | 26.4 σ = 1.8 | −13.3 |
| | 100 nM | 19.9 σ = 1.6 | 26.4 σ = 1.8 | −24.6 |
| | 250 nM | 20.9 σ = 1.4 | 26.4 σ = 1.8 | −20.8 |
| | 500 nM | 21.2 σ = 1.7 | 26.4 σ = 1.8 | −19.7 |
| | 1 µM | 20 σ = 1.2 | 26.4 σ = 1.8 | −24.2 |
| SEQ ID NO. 5 | 10 nM | 23.5 σ = 0.7 | 26.4 σ = 1.8 | −10.9 |
| | 100 nM | 19.3 σ = 0.9 | 26.4 σ = 1.8 | −26.9 |
| | 250 nM | 17.9 σ = 1.7 | 26.4 σ = 1.8 | −32.2 |
| | 500 nM | 20.5 σ = 0.6 | 26.4 σ = 1.8 | −22.4 |
| | 1 µM | 21.3 σ = 0.8 | 26.4 σ = 1.8 | −19.3 |

TABLE 2-continued

| Identification numbers and concentrations of the oligonucleotides tested | | Reaction rates $10^{-4}$ OD units/min | Reaction rates (control without oligonucleotide) | % variation compared to control |
|---|---|---|---|---|
| SEQ ID NO. 6 | 10 nM | 20.7 σ = 1.8 | 26.4 σ = 1.8 | −21.6 |
| | 100 nM | 22.0 σ = 0.6 | 26.4 σ = 1.8 | −16.7 |
| | 250 nM | 20.1 σ = 2.5 | 26.4 σ = 1.8 | −23.9 |
| | 500 nM | 18.7 σ = 2.6 | 26.4 σ = 1.8 | −29.2 |
| | 1 µM | 20.5 σ = 1.1 | 26.4 σ = 1.8 | −22.4 |
| SEQ ID NO. 7 | 10 nM | 26.6 σ = 2.2 | 25.0 σ = 0.9 | +6.4 |
| | 100 nM | 25.3 σ = 1.1 | 25.0 σ = 0.9 | +1.2 |
| | 250 nM | 23.8 σ = 1.3 | 25.0 σ = 0.9 | −4.8 |
| | 500 nM | 21.7 σ = 0.9 | 25.0 σ = 0.9 | −13.2 |
| | 1 µM | 22.6 σ = 0.7 | 25.0 σ = 0.9 | −9.6 |
| SEQ ID NO. 8 | 10 nM | 24.1 σ = 0.1 | 25.0 σ = 0.9 | −3.6 |
| | 100 nM | 23.7 σ = 0.6 | 25.0 σ = 0.9 | −2.5 |
| | 250 nM | 25.1 σ = 1.0 | 25.0 σ = 0.9 | +0.4 |
| | 500 nM | 23.4 σ = 0.6 | 25.0 σ = 0.9 | −6.4 |
| | 1 µM | 23.7 σ = 0.2 | 25.0 σ = 0.9 | −5.2 |
| SEQ ID NO. 9 | 10 nM | 27.1 σ = 0.7 | 25.0 σ = 0.9 | +8.4 |
| | 100 nM | 22.3 σ = 0.6 | 25.0 σ = 0.9 | −10.8 |
| | 250 nM | 22.6 σ = 0.2 | 25.0 σ = 0.9 | −9.6 |
| | 500 nM | 23.2 σ = 0.5 | 25.0 σ = 0.9 | −7.2 |
| | 1 µM | 25.0 σ = 0.7 | 25.0 σ = 0.9 | 0 |
| SEQ ID NO. 10 | 10 nM | 26.4 σ = 0.9 | 25.0 σ = 0.9 | +5.6 |
| | 100 nM | 24.9 σ = 0.5 | 25.0 σ = 0.9 | −0.4 |
| | 250 nM | 23.1 σ = 0.3 | 25.0 σ = 0.9 | −7.6 |
| | 500 nM | 23.3 σ = 0.6 | 25.0 σ = 0.9 | −6.8 |
| | 1 µM | 26.9 σ = 0.7 | 25.0 σ = 0.9 | +7.6 |
| SEQ ID NO. 11 | 10 nM | 25.7 σ = 0.9 | 25.0 σ = 0.9 | +2.8 |
| | 100 nM | 24.8 σ = 0.3 | 25.0 σ = 0.9 | −0.8 |
| | 250 nM | 25.8 σ = 0.7 | 25.0 σ = 0.9 | +3.2 |
| | 500 nM | 22.1 σ = 4.4 | 25.0 σ = 0.9 | −11.6 |
| | 1 µM | 23.9 σ = 0.8 | 25.0 σ = 0.9 | −4.4 |
| SEQ ID NO. 12 | 50 nM | 34.6 σ = 1.0 | 32.5 σ = 1.4 | +6.5 |
| | 100 nM | 33.2 σ = 0.7 | 32.5 σ = 1.4 | +2.2 |
| | 150 nM | 33.9 σ = 0.7 | 32.5 σ = 1.4 | +4.3 |
| SEQ ID NO. 13 | 50 nM | 33.5 σ = 1.2 | 32.5 σ = 1.4 | +3.1 |
| | 100 nM | 36.3 σ = 0.6 | 32.5 σ = 1.4 | +11.7 |
| | 150 nM | 34.0 σ = 1.2 | 32.5 σ = 1.4 | +4.6 |

It clearly emerges emerges from the results which appear in Table 2 that treating the melanocyte cultures with the oligonucleotides of the invention (SEQ ID NO. 1 to SEQ ID NO. 11) leads to a decrease in the reaction rate for the dopa oxidase activity. This decrease is particularly clear for the oligonucleotides SEQ ID NO. 1 to SEQ ID NO. 6.

On other hand, for the oligonucleotides tested by way of comparison with respect to the oligonucleotide SEQ ID NO. 2, namely the "sense control " SEQ ID NO. 12 and the "scrambled control" SEQ ID NO. 13, an increase in the reaction rate for the dopa oxidase activity is noted at each of the concentrations tested. For example, at the concentration of 100 nM, the reaction rate increases by 2.2% and by 11.7%, respectively, for the "sense control" and the "scrambled control", whereas it decreases by 28.8% in the case of the antisense oligonucleotide SEQ ID NO. 2 according to the invention.

It may be deduced from the latter observation that the activity of the oligonucleotides of the invention, which decrease the reaction rate for the dopa oxidase activity, is due to the specific hybridization of the oligonucleotide with the target messenger RNA encoding tyrosinase or that encoding TRP-1.

As a result, this oligonucleotide/mRNA interaction will prevent the translation of the information carried by the targeted messenger RNA and therefore lead to a decrease in the intracellular expression of tyrosinase, or of TRP-1, depending on the antisense sequence used. In other words, this interaction will decrease the neosynthesis of tyrosinase or of TRP-1. Because of the natural renewal of these enzymes, this leads to a decrease in the amount of tyrosinase and of TRP-1 in the cells and, consequently, a decrease in the activity of these enzymes in keeping with the synthesis of melanin. In fact, the oligonucleotides of the invention act by decreasing the renewal of tyrosinase and TRP-1, instead of acting on the tyrosinase already present in the melanocytes.

The consequence of this action on the melanocytes is that the capacity of these cells to synthesize melanin is reduced, hence, depending on the case and the individuals concerned, the production of a bleaching or depigmenting effect.

EXAMPLE 3

Depigmenting Effect of an Oligonucleotide According to the Invention on Normal Human Melanocytes from a Mulatto Adult Donor The melanocytes used here are obtained from skin from the thighs of a mulatto adult donor. The skin fragments are rinsed with PBS (Gibco, Paisley, GB) and then washed with 70% ethanol (V/V) diluted to 50% in PBS. After washing with PBS, the skin fragments are scraped using a corn cutter. The pieces obtained are scraped in 0.05% trypsin (Difco Laboratories, West Molesy, GB) for one hour at 37° C. in order to allow them to dissociate. The epidermis is then recovered in E-199 medium (Gibco, Paisley, GB) containing 10% of foetal calf serum (FCS, Gibco, Paisley, GB). After homogenization and elimination of the fragments of horny layer floating at the surface, the cell suspension is filtered and then centrifuged. The cell pellet obtained is taken up in the Medium 1 described in Example 2. The cells are counted and the cell viability is measured on a Thoma cell using the trypan blue exclusion assay. The epidermal cells are finally seeded in Medium 1, in flasks, in a proportion of 80 000 cells/cm$^2$. The cultures are maintained at 37° C. in an atmosphere which is saturated with humidity, and with 5% of $CO_2$.

Medium 1 is replaced with Medium 6, the composition of which is specified in the table below, in which B-FGF denotes a basic fibroblast growth factor, and PdBu denotes phorbol 12,13-dibutyrate.

| COMPOSITION OF MEDIUM 6 | | |
| --- | --- | --- |
| Compounds | Supplier, reference | Final concentration in the medium |
| E-199 medium | Gibco, 31150-022 | q.s. for 100% (v/v) |
| Insulin | Sigma, H-0888 | 0.5 µg/ml |
| EGF | Sigma, E-4127 | 10 ng/ml |
| B-FGF | Gibco, 13256-029 | 10 ng/ml |
| PdBu | Sigma, P-1269 | 0.25 µg/ml |
| Calcium chloride | Prolabo, 22317297 | 1.8 mM |

This medium is renewed every 48 hours for one to two weeks.

After this selection of melanocytes, NHM proliferation is promoted by replacing Medium 6 with Medium 7.

Medium 7 consists of 10% of Medium C and 90% of Medium A described above, supplemented with PdBu (Sigma, P-1269), the final concentration of which in the medium is 0.25 µg/ml.

| COMPOSITION OF MEDIUM C | | |
| --- | --- | --- |
| Compounds | Supplier, reference | Final concentration in the medium |
| E-199 medium | Gibco, 31150-022 | q.s. for 100% (v/v) |
| Foetal calf serum | Gibco, 10099-133 | 10% (v/v) |
| L-glutamine | Gibco, 25030-024 | 2 mM |
| IBMX | Sigma, I-5879 | $10^{-4}$ M |
| Geneticin | Gibco, 066-01811Y | 100 µg/ml |

At this stage, the cell population obtained is pure. It consists exclusively of NHMs.

The NHMs are seeded in 96-well microplates (Falcon, Franklin Lakes, N.J., USA) in Medium 6. After 24 h, the medium is replaced with Medium 8, which will be used throughout the end of this study. The composition of Medium 8 is described below.

| COMPOSITION OF MEDIUM 8 | | |
| --- | --- | --- |
| Compounds | Supplier, reference | Final concentration in the medium |
| MCDB-153 medium | Sigma, M-7403 | q.s. for 100% (v/v) |
| Foetal calf serum | Gibco, 10099-133 | 2% (v/v) |
| Insulin | Sigma, I-6634 | 5 µg/ml |
| Transferrin | Sigma | 10 µg/ml |
| α-Tocopherol | Sigma, T1157 | 1 µg/ml |
| Penicillin/ streptomycin | Sigma, P4333 | 0.4% (v/v) |

The oligonucleotide SEQ ID NO. 2 is added extemporaneously to the study medium, at concentrations of 50 nM, 100 nM, 250 nM, 500 nM and 1 µM. The treatments are carried out each day for 7 days. For each concentration, 6 assays are performed.

Measurement of Reaction Rates for the Dopa Oxidase Activity:

At the end of these treatments divided up over 7 days, the dopa oxidase activity is measured. These measurements are performed in the same way as in Example 2. The reaction rates are calculated and expressed as $10^{-4}$ OD units/min.

The results obtained for the cultures treated with the oligonucleotide SEQ ID NO. 2 and for the nontreated control cultures are given in Table 3 (σ: standard deviation).

TABLE 3

| Concentrations of the oligonucleotide SEQ ID NO. 2 | Reaction rates | Reaction rates (control without oligonucleotide) | % variation compared to control |
| --- | --- | --- | --- |
| 50 nM | 33.8 σ = 3.4 | 33.0 σ = 3.5 | +2.4 |
| 100 nM | 29.8 σ = 1.3 | 33.0 σ = 3.5 | −9.7 |
| 250 nM | 29.6 σ = 2.2 | 33.0 σ = 3.5 | −10.3 |
| 500 nM | 28.3 σ = 1.5 | 33.0 σ = 3.5 | −14.2 |
| 1 µm | 27.6 σ = 2.9 | 33.0 σ = 3.5 | −16.3 |

According to the results above, it is observed that, from quite a low concentration of oligonucleotide (100 nM) and above this concentration, the reaction rate for the dopa oxidase activity decreases very substantially.

Thus, as already explained in the conclusion of Example 2, the oligonucleotides according to the invention decrease the capacity of the melanocytes to synthesize melanin. It is demonstrated in the present assay that this decrease is independent of the genetic characteristics of the person concerned.

In the present example, since it involves a mulatto donor having a basic pigmentation corresponding to a dark skin colour, the use of an oligonucleotide according to the invention will lead to a bleaching effect, i.e. to a lightening of the skin complexion.

EXAMPLE 4

Study of the Inhibition of UV-Induced Melanogenesis, on Normal Human Melanocytes, by an Oligonucleotide According to the Invention Subsequent to the results of the examples above, the objective of the present assay is to verify whether the oligonucleotides of the invention are also active when the melanocytes are activated by a stimulation, in this case by UVB ultraviolet irradiation (280–320 nm). In other words, it involves evaluating the capacity of the oligonucleotides to decrease the dopa oxidase activity of melanocytes independently of the stimulation of melanogenesis.

To this effect, the assay relates to melanocytes from an adult donor of Caucasian type. The melanocytes used here are obtained from skin from mammaplasty. The technique for obtaining these melanocytes is the same as that used and described in Example 3.

The experiment is carried out in 35 mm dishes. The melanocytes are seeded in 35 mm dishes (Falcon, Franklin Lakes, N.J. USA) in a proportion of 250 000 cells and 2 ml of Medium 8 per dish. The composition of Medium 8 is described in Example 3. The treatments with the oligonucleotides SEQ ID NO. 2 and also the UVB irradiation (Bio-Energie, Vilbert-Lourmat, Marne-la-Vallée, France) at 8 mJ/cm$^2$ begin 24 h after seeding.

Before each UVB irradiation, the NHMs are placed in PBS (2 ml/dish). After irradiation, the cells are again placed in 2 ml of Medium 8 which may or may not contain the oligonucleotide SEQ ID NO. 2.

The oligonucleotide SEQ ID NO. 2 is added extemporaneously to the study medium (Medium 7 of Example 3), at concentrations of 100 nM, 250 nM and 500 nM.

These treatments with the oligonucleotide are carried out each day for 9 days. The irradiation takes place each day, except for days 5 and 6. For each concentration, 3 assays are performed.

Measurement of Reaction Rates for the Dopa Oxidase Activity:

At the end of these treatments, i.e. 9 days of treatment with the oligonucleotide and 7 rounds of irradiation, the dopa oxidase activity is measured.

To this effect, the NHMs are detached from the 35 mm dishes using 500 μl of 0.1% trypsin-0.05% EDTA and then taken up in 1.5 ml of E-199 medium without phenol red (Gibco) and supplemented with 10% of foetal calf serum. An aliquot portion of this cell suspension is used to count the cells, and another is centrifuged and the melanocyte pellet obtained is taken up in 50 μl of lysis buffer in order to measure the reaction rate for the dopa oxidase as described in Example 2.

The reaction rates for the dopa oxidase activity are calculated and expressed as $10^{-4}$ OD units/min/$10^6$ NHMs. The results obtained are given in Table 4 (σ: standard deviation).

TABLE 4

| Cell culture treatments: UVB irradiation/ concentration of oligonucleotide SEQ ID NO. 2 | Reaction rate | % variation compared to non-irradiated control | % variation compared to irradiated control |
| --- | --- | --- | --- |
| No irradiation/no oligonucleotide (non-irradiated control) | 368.2 σ = 19.9 | 0 | |
| Irradiation/no oligonucleotide (irradiated control) | 409.1 σ = 32.6 | +11.1% | 0 |
| Irradiation/100 nM | 328.1 σ = 44.8 | | −19.8% |
| Irradiation/250 nM | 325.3 σ = 43.1 | | −20.5% |
| Irradiation/500 nM | 327.4 σ = 49.5 | | −20% |

The results above clearly demonstrate that the oligonucleotides according to the invention very substantially decrease the reaction rate for the dopa oxidase activity in the case of melanocytes stimulated under the effect of UVB radiation.

Thus, the oligonucleotides according to the invention not only decrease the capacity of melanocytes in a state of basal activity to synthesize melanin, as was demonstrated in the previous examples, but they also decreased this capacity for melanocytes in the activated state. These oligonucleotides may therefore also be used in particular for preventing or attenuating a pigmentation triggered by the ultraviolet radiation present in sunlight.

EXAMPLE 5

Powder for Lightening the Complexion of the Face

| | |
| --- | --- |
| Microcellulose | 20.00% |
| Sodium lauryl sulphoacetate | 15.00% |
| Oligonucleotide (SEQ ID NO. 5) (phosphodiester) | 1.00% |
| Fragrance, colorants, preserving agents | q.s. |
| Talc | q.s. for 100% |

This powder has a double action. It enables the skin to be cleansed and, in addition, when used regularly for a few days, it enables the complexion to be lightened. It may be applied to the skin of the face one to two times a day.

EXAMPLE 6

Depigmenting Day Emulsion-Gel for the Face

| | |
| --- | --- |
| Glycerol | 5.00% |
| Caprylic/capric/succinic triglycerides | 5.00% |
| Octyl methoxycinnamate | 1.00% |
| Dimethicone copolyol | 0.50% |
| Acrylates/$C_{10}$–$C_{30}$ alkylacrylate crosspolymer | 0.50% |
| Oligonucleotide SEQ ID NO. 3 (phosphodiester) | 0.01% |
| Neutralizing agent | q.s. |
| Preserving agents, fragrance, colorants | q.s. |
| Water | q.s. for 100% |

Certain individuals subjected to more or less intense radiation from daylight, or even from direct sunlight, wish to conserve a light complexion and avoid the appearance of pigmented blemishes. The use of the emulsion-gel above will make it possible to achieve this aim. This composition is applied to the face generally in the morning. It acts both preventively and curatively on the pigmentation, which may or may not be even, of the face.

EXAMPLE 7

SPF 30 Protective Fluid for Preventing Pigm ntary Blemishes

| | |
|---|---|
| Volatile pentacyclomethicone | 49.00% |
| Titanium dioxide | 15.00% |
| Octyl methoxycinnamate | 7.50% |
| Glycerol | 5.00% |
| Phenyltrimethicone | 5.00% |
| Dimethicone copolyol | 3.00% |
| Polymethyl methacrylate | 2.50% |
| Butylmethoxydibenzoylmethane | 1.00% |
| Oligonucleotide SEQ ID NO. 2 (phosphodiester) | 0.1% |
| Neutralizing agent, fragrance, preserving agents, antioxidants | q.s. |
| Water | q.s. for 100% |

This composition is to be used for preventing the appearance of pigmentary blemishes in individuals predisposed to this phenomenon, before exposure to intense radiation from the sun. It should be noted that the presence of a high concentration of sunscreen makes it possible to compensate for the decrease in natural protection which is a consequence of the drop in the melanin level.

EXAMPLE 8

Depigmenting Face Cream

| | |
|---|---|
| Glyceryl stearate + Peg-100 stearate | 5.00% |
| Hydrogenated polyisobutene | 4.00% |
| Magnesium ascorbyl phosphate | 3.30% |
| Glyceryl tricaprylate/caprate | 3.00% |
| Squalane | 3.00% |
| Glycerol | 2.00% |
| Beeswax | 1.50% |
| Cetearyl octanoate | 1.50% |
| Cetyl alcohol | 1.00% |
| Stearyl alcohol | 1.00% |
| Dimethicone | 1.00% |
| Xanthan gum | 0.30% |
| Ethylenediaminetetracetic acid | 0.20% |
| Citric acid | 0.10% |
| Sodium citrate | 0.10% |
| Oligonucleotide SEQ ID NO. 6 (phosphodiester) | 0.10% |
| Neutralizing agent, fragrance, preserving agents | q.s. |
| Water | q.s. for 100% |

The use of this cream makes it possible to treat irregularities of the skin pigmentation by attenuating or eliminating senescent blemishes or actinic pigmentary blemishes. It makes the skin colour homogeneous and lightens the complexion.

EXAMPLE 9

Face Lotion for Lightening the Complexion

| | |
|---|---|
| Ethyl alcohol | 30.00% |
| PPG-3 myristyl ether | 5.00% |
| Glycerol | 2.00% |
| Carbomer | 0.20% |
| Polysorbate 20 | 0.20% |
| Oligonucleotide SEQ ID NO. 4 (phosphorothioate) | 0.01% |
| Neutralizing agent, fragrance, preserving agents | q.s. |
| Water | q.s. for 100% |

This lotion for lightening the complexion is used after make-up has been removed and the skin has been cleaned.

EXAMPLE 10

Face Serum for Lightening the Complexion

| | |
|---|---|
| Water | q.s. for 100% |
| Glycerol | 2% |
| Tetrasodium EDTA | |
| Citric acid | q.s. for pH 6 |
| Trisodium citrate | |
| Xanthan gum | 0.25% |
| Polyacrylamide, $C_{13}/C_{14}$ isoparaffin, laureth-7 | 0.5% |
| Dimethicone copolyol | 0.25% |
| Oligonucleotide SEQ ID NO. 2 (phosphodiester) | 0.1% |
| Fragrance, colorant, preserving agent | q.s. |

One drop of this very concentrated serum composition is applied to the face generally before the application of a face cream. This serum is conventionally used as treatments of one to two weeks in order to obtain or maintain a lightening of the complexion.

EXAMPLE 11

Hair Lotion for Lightening the Head of Hair

| | |
|---|---|
| Water | q.s. for 100% |
| Alcohol | 50% |
| Panthenylethyl ether | 0.5% |
| DL-α-tocopherol acetate | 0.2% |
| Polysorbate 60 | 1% |
| Oligonucleotide SEQ ID NO. 1 (phosphorothioate) | 0.01% |
| Fragrance | 0.2% |
| Glycerol | 0.5% |
| Colorant | q.s. |

This lotion is applied to the hair in the morning and evening for as long as is necessary to obtain a gradual lightening of the head of hair. This period of time is generally several weeks.

EXAMPLE 12

Hand Cream (Anti-Blemish Gel-Cream)

| | |
|---|---|
| Caprylic/capric digilyceryl succinate | 6% |
| Octyl octanoate | 2.5% |
| Octyl methoxycinnamate | 6% |
| Oligonucleotide SEQ ID NO. 5 (phosphodiester) | 0.001% |
| Phenyl trimethicone | 2.5% |
| Benzophenone-3 | 0.5% |
| Sodium hyaluronate | 0.05% |
| Xanthan gum | 0.2% |

-continued

| | |
|---|---|
| Acrylates/$C_{10}$–$C_{30}$ alkyl acrylate copolymer | 0.5% |
| Glycerol | 2% |
| PEG 150 | 3% |
| Neutralizing agents, colorants, fragrance, preserving agents | q.s. |
| Purified water | q.s. for 100% |

This cream should be applied directly to the senescent blemishes (senile lentigo) of the hands in order to attenuate the coloration thereof.

The invention claimed is:

1. An oligonucleotide up to 25 bases in length having the sequence—(SEQ ID NO: 6) 5'-AGGAACTGGCTAATTG-GAGT-3'.

2. The oligonucleotide defined by claim 1, comprising one or more chemical modifications to its sugar components, wherein the sugar component comprises a 2'—O-fluoro or 2'—O-alkyl substituent.

3. The oligonucleotide defined by claim 1, comprising one or more chemical modifications to its sugar components, wherein the sugar component comprises a 2'—O-fluoro or 2'—O-alkyl substituent, wherein the 2'—O-alkyl substituent, is a 2'—O-ethyloxymethyl or 2'—O-methyl substituent.

4. The oligonucleotide defined by claim 1, comprising one or more chemical modifications of its nucleobase components or its internucleotide backbone.

5. The oligonucleotide defined by claim 1, comprising one or more chemical modifications of its nucleobase components or its internucleotide backbone, wherein some of the phosphodiester groups of its internucleotide backbone are replaced with methyl phosphonate groups.

6. The oligonucleotide defined by claim 1, comprising one or more chemical modifications of its nucleobase components or its internucleotide backbone, wherein all the phosphodiester groups of its internucleotide backbone are replaced with phosphorothioate groups.

7. The oligonucleotide defined by claim 1, comprising one or more chemical modifications of its nucleobase components or its internucleotide backbone, wherein all the phosphodiester groups of its internucleotide backbone are replaced with methyl phosphonate groups.

8. The oligonucleotide defined by claim 1, comprising one or more chemical modifications of its nucleobase components or its internucleotide backbone, wherein the phosphodiester groups are entirely or partly replaced with components selected from the group consisting of phosphorothioate groups and methyl phosphonate groups.

9. A cosmetic or dermatological composition containing the oligonucleotide according to claim 1 and a cosmetically or dermatologically acceptable medium.

10. A cosmetic or dermatological composition containing the oligonucleotide defined by claim 1, and a cosmetically or dermatologically acceptable medium, wherein the oligonucleotide(s) represent(s) 0.00001% to 10% of the total weight of the composition.

11. The oligonucleotide defined by claim 1, comprising one or more chemical modifications to its sugar components, wherein the sugar component comprises a 2'—O-fluoro or 2'—O-alkyl substituent, and comprising one or more chemical modifications of its nucleobase components or its internucleotide backbone.

12. The oligonucleotide defined by claim 1, comprising one or more chemical modifications of its nucleobase components or its internucleotide backbone, wherein some of the phosphodiester groups of its internucleotide backbone are replaced with phosphorothioate group.

13. The oligonucleotide defined by claim 1, comprising one or more chemical modifications to its sugar components. wherein the sugar component comprises a 2'—O-fluoro or 2'—O-alkyl substituent, and comprising one or more chemical modifications of its nucleobase components or its internucleotide backbone, wherein some of the phosphodiester groups of its internucleotide backbone are replaced with phosphorothioate group.

14. The oligonucleotide defined by claim 1, comprising one or more chemical modifications to its sugar components, wherein the sugar component comprises a 2'—O-fluoro or 2'—O-alkyl substituent, and comprising one or more chemical modifications of its nucleobase components or its internucleotide backbone, wherein some of the phosphodiester groups of its internucleotide backbone are replaced with methyl phosphonate groups.

15. The oligonucleotide according to claim 13, wherein all the phosphodiester groups are replaced with phosphorothioate groups.

16. The oligonucleotide defined by claim 1, comprising one or more chemical modifications to its sugar components. wherein the sugar component comprises a 2'—O-fluoro or 2'—O-alkyl substituent, and comprising one or more chemical modifications of its nucleobase components or its internucleotide backbone, wherein all the phosphodiester groups of its internucleotide backbone are replaced with methyl phosphonate groups.

17. The oligonucleotide defined by claim 1, comprising one or more chemical modifications to its sugar components, wherein the sugar component comprises a 2'—O-fluoro or 2'—O-alkyl substituent, and comprising one or more chemical modifications of its nucleobase components or its internucleotide backbone, wherein the phosphodiester groups are entirely or partly replaced with components selected from the group consisting of phosphorothioate groups and methyl phosphonate groups.

18. A cosmetic or dermatological composition containing the oligonucleotide according to claim 2 and a cosmetically or dermatologically acceptable medium.

19. A cosmetic or dermatalogical composition containing the oligonucleotide according to claim 4 and a cosmetically or dermatologically acceptable medium.

20. The oligonucleotide defined by claim 1, comprising one or more chemical modifications to its sugar components, wherein the sugar component comprises a 2'—O-fluoro or 2'—O-alkyl substituent, and a cosmetically or dermatologically acceptable medium wherein the oligonucleotide(s) represent(s) 0.00001% to 10% of the total weight of the composition.

21. The cosmetic or dermatalogical composition defined by claim 19, wherein the oligonucleotide(s) represent(s) 0.00001% to 10% of the total weight of the composition.

22. A cosmetic or dermatological composition containing the oligonucleotide defined by claim 1, and a cosmetically or dermatologically acceptable medium, wherein the oligonucleotide(s) represent(s) 0.0003% to 3% of the total weight of the composition.

23. A cosmetic or dermatological composition containing the oligonucleotide defined by claim 1 comprising one or more chemical modifications to its sugar components, wherein the sugar component comprises a 2'—O-fluoro or 2'—O-alkyl substituent and a cosmetically or dermatologically acceptable medium, wherein the oligonucleotide represents 0.0003% to 3% of the total weight of the composition.

24. A cosmetic or dermatological composition containing the oligonucleotide defined by claim 1 comprising one or more chemical modifications of its nucleobase components or its internucleotide backbone, and a cosmetically or dermatologically acceptable medium, wherein the oligonucleotide represents 0.0003% to 3% of the total weight of the composition.

* * * * *

SEQUENCE LISTING

```
<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<223> OTHER INFORMATION: Antisense oligonucleotide complementary to the
      nt sequence 111-92 of the cDNA of the gene encoding human
      tyrosinase-related-protein (TRP - Genbank locus HSTYRRP).

<400> SEQUENCE: 1
gcaaaacaaa gacctggttt                                                20

<210> SEQ ID NO 2
<211> LENGTH: 23
<212> TYPE: DNA
<213> ORGANISM: Artificial Sequence
<220> FEATURE:
<223> OTHER INFORMATION: Antisense oligonucleotide complementary to the
      nt sequence 102-83 of the cDNA of the gene encoding human
      tyrosinase-related-protein (TRP - Genbank locus HSTYRRP).

<400> SEQUENCE: 2
agacctggtt tgcagctctt art                                            23

<210> SEQ ID NO 3
<211> LENGTH: 20
<212> TYPE: DNA
<213> ORGANISM: Artificial Sequence
<220> FEATURE:
<223> OTHER INFORMATION: Antisense oligonucleotide complementary to the
      nt sequence 127-108 of the cDNA of the gene encoding human
      tyrosinase-related-protein (TRP - Genbank locus HSTYRRP).

<400> SEQUENCE: 3
tgcttgaaat aagagtgcaa                                                20

<210> SEQ ID NO 4
<211> LENGTH: 20
<212> TYPE: DNA
<213> ORGANISM: Artificial Sequence
<220> FEATURE:
<223> OTHER INFORMATION: Antisense oligonucleotide complementary to the
      nt sequence 53-54 of the cDNA of the gene encoding human
      tyrosinase-related-protein (TRP - Genbank locus HSTYRRP).

<400> SEQUENCE: 4
aaaatccagc tcacaatcct                                                20
```

<210> SEQ ID NO 5
<211> LENGTH: 20
<212> TYPE: DNA
<213> ORGANISM: Artificial Sequence
<220> FEATURE:
<223> OTHER INFORMATION: Antisense oligonucleotide complementary to the
      nt sequence 141-122 of the cDNA of the gene encoding human
      tyrosinase-related-protein (TRP - Genbank locus HSTYRRP).

<400> SEQUENCE: 5
aggagcactc attctgcttg                                             20

<210> SEQ ID NO 6
<211> LENGTH: 20
<212> TYPE: DNA
<213> ORGANISM: Artificial Sequence
<220> FEATURE:
<223> OTHER INFORMATION: Antisense oligonucleotide complementary to the
      nt sequence 475-457 of the cDNA of the gene encoding human
      tyrosinase (Genbank locus HUMTYRA).

<400> SEQUENCE: 6
aggaactggc taattggagt                                             20

<210> SEQ ID NO 7
<211> LENGTH: 20
<212> TYPE: DNA
<213> ORGANISM: Artificial Sequence
<220> FEATURE:
<223> OTHER INFORMATION: Antisense oligonucleotide complementary to the
      nt sequence 485-466 of the cDNA of the gene encoding human
      tyrosinase (Genbank locus HUMTYRA).

<400> SEQUENCE: 7
caaggtctgc aggaactggc                                             20

<210> SEQ ID NO 8
<211> LENGTH: 20
<212> TYPE: DNA
<213> ORGANISM: Artificial Sequence
<220> FEATURE:
<223> OTHER INFORMATION: Antisense oligonucleotide complementary to the
      nt sequence 490-471 of the cDNA of the gene encoding human
      tyrosinase (Genbank locus HUMTYRA).

<400> SEQUENCE: 8
cctcacaagg tctgcaggaa                                             20

<210> SEQ ID NO 9
<211> LENGTH: 20
<212> TYPE: DNA
<213> ORGANISM: Artificial Sequence
<220> FEATURE:
<223> OTHER INFORMATION: Antisense oligonucleotide complementary to the
      nt sequence 1332-1313 of the cDNA of the gene encoding human
      tyrosinase (Genbank locus HUMTYRA).

<400> SEQUENCE: 9
ctacagacaa tctgccaaga                                             20

<210> SEQ ID NO 10
<211> LENGTH: 20
<212> TYPE: DNA
<213> ORGANISM: Artificial Sequence
<220> FEATURE:

-continued

```
<223> OTHER INFORMATION: Antisense oligonucleotide complementary to the
      nt sequence 506-487 of the cDNA of the gene encoding human
      tyrosinase (Genbank locus HUMTYRA).

<400> SEQUENCE: 10
gcattcttcc tctagtcctc                                                    20

<210> SEQ ID NO 11
<211> LENGTH: 20
<212> TYPE: DNA
<213> ORGANISM: Artificial Sequence
<220> FEATURE:
<223> OTHER INFORMATION: Antisense oligonucleotide complementary to the
      nt sequence 5875-5856 of the DNA encoding human
      tyrosinase-related-protein-1 (TRP1 - Genbank locus AF 001295).

<400> SEQUENCE: 11
ttccagtacc tcacaatcct                                                    20

<210> SEQ ID NO 12
<211> LENGTH: 20
<212> TYPE: DNA
<213> ORGANISM: Artificial Sequence
<220> FEATURE:
<223> OTHER INFORMATION: Antisense control for sequence ID No. 2.

<400> SEQUENCE: 12
ttctcgacgt ttggtccaga                                                    20

<210> SEQ ID NO 13
<211> LENGTH: 20
<212> TYPE: DNA
<213> ORGANISM: Artificial Sequence
<220> FEATURE:
<223> OTHER INFORMATION: Random combination of sequence ID No. 2.

<400> SEQUENCE: 13
acgtttctcg cctagtgatg                                                    20
```